(12) United States Patent
Cashman

(10) Patent No.: US 8,906,943 B2
(45) Date of Patent: *Dec. 9, 2014

(54) SYNTHETIC COMPOUNDS AND METHODS TO DECREASE NICOTINE SELF-ADMINISTRATION

(76) Inventor: John R. Cashman, San Diego, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 13/204,095

(22) Filed: Aug. 5, 2011

(65) Prior Publication Data

US 2012/0196905 A1 Aug. 2, 2012

Related U.S. Application Data

(60) Provisional application No. 61/400,876, filed on Aug. 5, 2010.

(51) Int. Cl.

| | | |
|---|---|---|
| A61K 31/4439 | (2006.01) |
| C07D 413/04 | (2006.01) |
| C07D 233/56 | (2006.01) |
| C07D 409/04 | (2006.01) |
| C07D 405/04 | (2006.01) |
| C07D 233/58 | (2006.01) |
| A61K 31/4174 | (2006.01) |
| A61K 31/4436 | (2006.01) |
| A61K 31/443 | (2006.01) |
| A61P 25/30 | (2006.01) |
| A61P 35/00 | (2006.01) |
| A61P 25/28 | (2006.01) |
| A61P 25/00 | (2006.01) |
| A61P 25/32 | (2006.01) |
| A61P 25/22 | (2006.01) |
| C07D 401/04 | (2006.01) |
| A61K 31/4427 | (2006.01) |

(52) U.S. Cl.
CPC ......... *A61K 31/4436* (2013.01); *A61K 31/4427* (2013.01); *A61K 31/4439* (2013.01)
USPC ....................................... 514/341; 546/272.7

(58) Field of Classification Search
USPC ..................... 514/341, 335.1, 340, 396, 336; 546/275.4, 272.1, 280.4, 272.7, 283.4; 548/346.1, 335.1
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,011,847 A | 4/1991 | Biftu et al. |
| 5,013,556 A | 5/1991 | Woodle et al. |
| 2006/0217389 A1 | 9/2006 | Sun et al. |
| 2008/0188467 A1 | 8/2008 | Wong et al. |
| 2008/0188527 A1 | 8/2008 | Cashman |

OTHER PUBLICATIONS

Buchwald et al., Long-term, continuous intravenous heparin administration by an implantable infusion pump in ambulatory patients with recurrent venous thrombosis. Surgery Oct. 1980;88(4):507-516.
During et al., Controlled release of dopamine from a polymeric brain implant: In vivo characterization. Ann. Neurol. Apr. 1989; 25(4):351-356.
Greenlee et al., An improved assay of 7-ethoxycoumarin O-deethylase activity: induction of hepatic enzyme activity in C57BL/6J and DBA/2J mice by phenobarbital, 3-methylcholanthrene and 2,3,7,8-tetrachlorodibenzo-p-dioxin. J Pharmacol Exp Ther, Jun. 1978;205(3):596-605.
Howard et al., Intracerebral drug delivery in rats with lesion-induced memory deficits. J. Neurosurg. Jul. 1989;71(1):105-112.
International Search Report and Written Opinion issued in PCT/US2011/046733 on Jan. 5, 2012.
Langer and Peppas, Chemical and Physical Structure of Polymers as Carriers for Controlled Release of Bioactive Agents: A Review. J. Macromol. Sci. Rev. Macromol. Chem. 1983; 23:61-126.
Langer, New methods of drug delivery. Science Sep. 28, 1990;249(4976):1527-1533.
Levy et al., Inhibition of calcification of bioprosthetic heart valves by local controlled-release diphosphonate. Science Apr. 12, 1985;228(4696):190-192.
Saudek et al., A preliminary trial of the programmable implantable medication system for insulin delivery. N. Engl. J. Med. Aug. 31, 1989;321(9):574-579.
Sefton, Implantable Pumps. CRC Crit. Ref. Biomed. Eng. 1987;14(3):201-240.
Su et al., Human cytochrome P450 CYP2A13: predominant expression in the respiratory tract and its high efficiency metabolic activation of a tobacco-specific carcinogen, 4-(methylnitrosamino)-1-(3-pyridyl)-1-butanone. Cancer Res. Sep. 15, 2000;60(18):5074-5079.
Treat et al., Liposome Encapsulated Doxorubicin Preliminary Results of Phase I and Phase II Trials. Liposomes in the Therapy of Infectious Disease and Cancer. Lopez-Berestein and Fidler eds., c.1989 Alan R. Liss, Inc; pp. 353-365.
Watkins et al., Blockade of nicotine self-administration with nicotinic antagonists in rats. Pharmacol Biochem Behavior Apr. 1999; 62(4):743-751.
Wermuth et al. "Glossary of Terms in Medicinal Chemistry" *Pure & Appl. Chem.* (1998), 70: 1129-1143.

*Primary Examiner* — Kendra D Carter
*Assistant Examiner* — Jason A Deck

(57) ABSTRACT

Methods and small molecule compounds for smoking and CNS disease harm reduction are provided. One example of a class of compounds that may be used is represented by the compound having the structure IA or IB in the form of free base or a pharmaceutically acceptable salt, hydrate or solvate thereof.

5 Claims, 2 Drawing Sheets

SYNTHETIC COMPOUNDS AND METHODS TO DECREASE NICOTINE SELF-ADMINISTRATION

CROSS-REFERENCES TO RELATED APPLICATIONS

The present application claims benefit to U.S. Provisional Application No. 61/400,876, filed Aug. 5, 2010 entitled "Cytochrome P-450 inhibitors decrease nicotine self-administration", the entire disclosure of which is incorporated herein by reference.

FIELD OF THE INVENTION

The present invention is in the field of pharmaceuticals and methods of treatment. In particular, the present invention is in the field of nicotine harm reduction agents. This invention provides pharmaceutical compositions and compounds useful in methods of inhibiting Cytochrome P450 2A6 and/or 2A13, decreasing the use of tobacco products, reducing the exposure to nicotine and the harmful by-products associated with the use of tobacco products, and reducing the harmful health and addictive effects associated with the use of such products. This invention is also useful in ameliorating other central nervous system diseases including Alzheimer's Disease, drug abuse, and other neurodegenerative diseases.

BACKGROUND OF THE DISCLOSURE

Even though over 1.1 billion persons worldwide smoke tobacco, current therapies to reduce smoking (e.g., the nicotine patch) have a low success rate after one year. There is an urgent need to develop a specific medication that can be used in conjunction with counseling and self-help programs to decrease smoking and save lives. Despite clear evidence that smoking tobacco is the leading cause of preventable death, almost one in four American adults smoke tobacco.

The major pharmacologically active chemical in tobacco is (S)-nicotine, which is primarily responsible for the pharmacological and behavioral effects of smoking including the stimulant and addictive properties. Nicotine causes complex central nervous system, behavioral, cardiovascular, endocrine, neuromuscular and metabolic effects in humans. Nicotine is one of the most addictive substances known. After administration to humans, nicotine undergoes extensive metabolism which reduces its pharmacological activity. The majority of such nicotine is metabolized via a cytochrome P-450 2A6 (CYP2A6)-dependent pathway to form nicotine $\Delta^{1',5'}$-iminium ion. In the presence of aldehyde oxidase, nicotine $\Delta^{1',5'}$-iminium ion is converted to cotinine. While cotinine can be further metabolized, cotinine has a long half-life and is a useful marker for both nicotine exposure and is also a functional indicator of CYP2A6 activity. In humans, a similar metabolic pathway occurs in the lung and respiratory system and utilizes a related enzyme system, CYP2A13.

Tobacco users (e.g., smokers) adjust their tobacco use to maintain a certain blood and brain level of nicotine. Recently, it has been observed that individuals with a decreased ability to metabolize nicotine (so-called poor metabolizers because they possess inactive alleles that code for the prominent enzyme that metabolizes nicotine and terminates its activity) are protected from becoming dependent on nicotine and have a reduced lung cancer risk. However, most smokers are not poor metabolizers of nicotine.

Reducing nicotine intake concomittantly reduces the intake or exposure of a tobacco user or smoker to other tobacco and tobacco smoke contaminants and their metabolites. Many of the metabolites and constituents of tobacco and tobacco smoke are toxic, for instance, the highly carcinogenic tobacco-specific N-nitrosamines. Such tobacco-specific N-nitrosamines play an important role in tobacco-related human lung cancer, due to their strong ability to induce lung tumorigenesis. It has been shown that hepatic CYP2A6 is involved in the mutagenic activation N-nitrosamines such as NNK, and that inhibition of CYP2A6 with a selective inhibitor, in turn, inhibits lung tumorigenesis in female A/J mice. In the lung, it is likely that CYP2A13 activates tobacco-related nitrosamines to mutagens and causes lung or other respiratory organ cancers.

The present invention meets these and other needs by providing novel compounds, pharmaceutical compositions, and methods of treatment which can be useful in treating tobacco addiction, reducing tobacco consumption, and in inhibiting CYP2A6 and/or CYP2A13 activity generally and, particularly, with respect to the metabolism of nicotine by CYP2A6 and/or CYP2A13. In vivo studies of two compounds administered to rats addicted with nicotine showed potency at reducing nicotine self-administration.

SUMMARY OF THE INVENTION

Disclosed herein are compounds of Formula I:

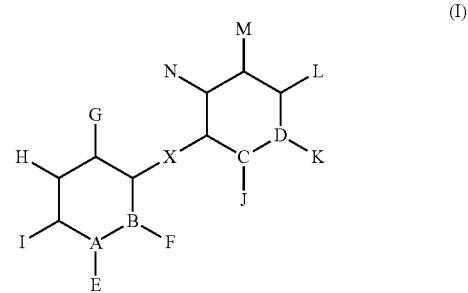

or a pharmaceutically acceptable salt, ester, amide, or prodrug thereof, wherein:

A, B, C, D, E and F constitute part of a 3-, 4-, 5- or 6-member ring system of unsaturated, partially unsaturated or saturated heterocyclic and carbocyclic rings, wherein the A, B, C, D, E and F ring system is optionally substituted with hydrido, acyl, halo, lower acyl, lower haloalkyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl, aryl, lower aralkylthio, lower alkylsulfinyl, lower alkylsulfonyl, aminosulfonyl, lower N-arylaminosulfonyl, lower arylsulfonyl, and lower N-alkyl-N-arylaminosulfonyl; wherein aryl of the A, B, C, D, E and F ring system is selected from phenyl, biphenyl, and naphthyl, 5-membered heteroaryl, and 6-membered heteroaryl, and is optionally substituted with one or two substituents selected from the group consisting of halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy; and wherein the acyl group is optionally substituted with a substituent selected from hydrido, alkyl, halo, and alkoxy;

wherein G, H, I, J, K, L M, N, O and P are independently selected from the group consisting of aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxyalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein the aryl of G, H, I, J, K, L M, N, O and/or P is optionally substituted and is selected from the group consisting of phenyl, biphenyl, naphthyl, 5-membered heteroaryl, and 6-membered heteroaryl.

Also disclosed are pharmaceutical compositions comprising the above compounds and a pharmaceutically acceptable carrier.

Also disclosed are methods for treating nicotine addiction, or reducing the risk of developing cancer, or alcoholism, or treating or preventing a neurodegenerative disease, or enhancing cognition, or treating or preventing a psychiatric disorder, or inducing a neuroprotective effect, in a subject, the method comprising identifying a subject in need thereof, and administering to the subject a therapeutically effective amount of a compound of Formula I, or a pharmaceutically acceptable salt, ester, or amide thereof.

In one aspect, the invention provides novel compounds, pharmaceutical compositions, and methods of treatment directed toward inhibiting the activity of Cytochrome P450 2A6 and/or 2A13 in a subject by administering Compounds of Formula I. In preferred embodiments, the subject is a human. In other preferred embodiments, the compound is a compound of Formula II. In still further embodiments, the compound is selective (based upon selectivity ratios) for Cytochrome P450 2A6 and/or 2A13 over at least one Cytochrome P450 enzyme selected from 3A4, 2E1, 2B6, 2C9, 2C19, and 2D6. In some further embodiments, the selectivity is at least 5-fold, 10-fold, or 20-fold over one or more of cytochrome P450 3A4, 2E1, 2B6, 2C9, 2C19, and 2D6. In still another embodiment, the compound selectively inhibits Cytochrome P450 2A6 over Cytochrome P450 3A4. In still other embodiments, the compound is not a substrate of, or is not significantly metabolized by, Cytochrome P450 2A6. In preferred embodiments, the biological half-time for the compound in human blood is typically at least 4 hours, 6 hours, 8 hours or 12 hours.

In another aspect, the invention provides methods of ameliorating the harmful effects (e.g., cancer) of tobacco use (e.g., smoking tobacco in cigarettes, cigars, or pipes; chewing tobacco) on health by administering a compound of Formula I or II to a tobacco user. In one embodiment, the administered compound interferes with the metabolism of constituents of tobacco or tobacco smoke (e.g., nicotine, nitrosamines) so as to reduce the formation of carcinogenic metabolites. In still other embodiments, the compound is selective (based upon selectivity ratios) for Cytochrome P450 2A6 and/or 2A13 over at least one Cytochrome P450 enzyme selected from 3A4, 2E1, 2B6, 2C9, 2C19, and 2D6. In some further embodiments, the selectivity is at least 5-fold, 10-fold, or 20-fold over one or more of cytochrome P450 3A4, 2E1, 2B6, 2C9, 2C19, and 2D6. In still another embodiment, the compound is selective for Cytochrome P450 2A6 and/or 2A13 over Cytochrome P450 3A4. In still other embodiments, the compound is not a substrate of, or is not significantly metabolized by, Cytochrome P450 2A6 and/or 2A13. In preferred embodiments, the biological half-time for the compound in human blood is typically at least 4 hours, 6 hours, 8 hours or 12 hours.

In still another aspect, the invention provides a method for modulating tobacco consumption or tobacco use in a human by administering to the human a Compound of Formula I or II. The tobacco may be in the form of a chewing tobacco, a cigarette, cigar or pipe tobacco. In some embodiments, the modulating is according to the amount of the tobacco product consumed or the amount of nicotine, or another constituent of tobacco or tobacco smoke, taken into the body. In still other embodiments, the compound is selective (based upon selectivity ratios) for Cytochrome P450 2A6 and/or 2A13 over at least one Cytochrome P450 enzyme selected from 3A4, 2E1, 2B6, 2C9, 2C19, and 2D6. In some further embodiments, the selectivity is at least 5-fold, 10-fold, or 20-fold over one or more of cytochrome P450 3A4, 2E1, 2B6, 2C9, 2C19, and 2D6. In still another embodiment, the compound is selective for Cytochrome P450 2A6 and/or 2A13 over Cytochrome P450 3A4. In yet other embodiments, the compound of Formula I or II is also capable of selectively modulating the activity of the acetylcholine nicotinic receptor. In still other embodiments, the compound is not a substrate of, or is not significantly metabolized by, Cytochrome P450 2A6 and/or 2A13. In preferred embodiments, the biological half-time for the compound in human blood is typically at least 4 hours, 6 hours, 8 hours or 12 hours. In one embodiment, a tobacco user is first phenotyped or genotyped with respect to Cytochrome P450 and the compound is administered to users who are not poor metabolizers.

DETAILED DESCRIPTION OF THE EMBODIMENTS

Definitions

Figure 1:
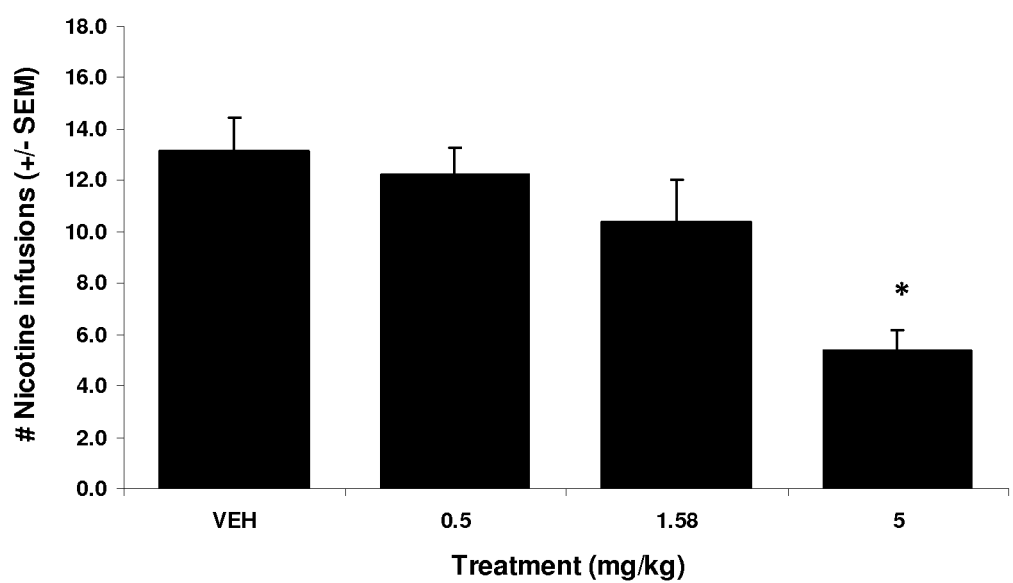
FIG. 1 is a graph showing the effects of compound 10 on IV self-administration of 0.03 mg/kg/infusions of nicotine under a fixed ratio 1 (FR1) schedule of reinforcement. Data are expressed as mean (±S.E.M.) number of infusions per session during LSD dose testing (n=8 rats). An ANOVA of the dose response of compound 10 revealed a significant effect of 10 on nicotine intake (F=15.5, df 3, 21, p<0.0001). Follow-up analysis (paired t-test) of individual doses of 10 revealed that a dose of 5 mg/kg was significantly different from vehicle-treated rats. *, p<0.05.

Unless defined otherwise, all technical and scientific terms used herein have the same meaning as commonly understood by one of ordinary skill in the art to which this invention belongs. Although any methods and material similar to those described herein can be used in the practice or testing of the present invention, only exemplary methods and materials are described. For purposes of the present disclosure, the following terms are defined below.

The terms "a," "an," and "the" include plural referents unless the context clearly dictates otherwise.

The term "hydrido" refers to a single hydrogen.

The term "alkyl" refers to saturated aliphatic groups including straight chain, branched chain, and cyclic groups, all of which may be optionally substituted. Suitable alkyl groups include methylene, methyl, ethyl, propyl and the like, and may be optionally substituted.

The term "alkenyl" refers to unsaturated groups which contain at least one carbon-carbon double bond and includes straight chain, branched chain, and cyclic groups, all of which may be optionally substituted.

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the ether —OR where R is alkyl, alkenyl, alkynyl, aralkyl.

The term "aryloxy" refers to the ether —OR where R is aryl or heteroaryl.

The term "alkenyloxy" refers to ether —OR where R is alkenyl.

The term "alkylthio" refers to —SR where R is alkyl, alkenyl, alkynyl, aryl, aralkyl.

The term "alkylthioalkyl" refers to an alkylthio group attached to an alkyl radical of about one to twenty carbon atoms through a divalent sulfur atom.

The term "alkylsulfinyl" refers to —S(O)R where R is alkyl, alkenyl, alkynyl, aryl, aralkyl.

The term "sulfonyl" refers to a —$SO_2$—R group where R is alkyl, alkenyl, alkynyl, aryl, aralkyl.

The terms "aminosulfonyl", "sulfamyl", "sulfonamidyl" refer to —$SO_2$NRR' where R and R' are independently selected from alkyl, alkenyl, alkynyl, aryl, aralkyl.

The term "hydroxyalkyl" refers to linear or branched alkyl radicals having one to about twenty carbon atoms any one of which may be substituted with a hydroxyl group.

The term "cyanoalkyl" refers to linear or branched alkyl radicals having one to about twenty carbon atoms any one of which could be substituted with one or more cyano groups.

The term "alkoxyalkyl" refers to alkyl groups having one or more alkoxy radicals attached to the alkyl group. The alkoxy radical may be further substituted with one or more halo atoms. Preferred haloalkoxy groups may contain one to twenty carbons.

The term "oximinoalkoxy" refers to alkoxy radicals having one to about twenty carbon atoms, any one of which may be substituted with an oximino radical.

The term "aryl" refers to aromatic groups which have at least one ring having conjugated "pi" electron system and includes carbocyclic aryl, biaryl, both of which may be optionally substituted.

The term "carbocyclic aryl" refers to groups wherein the ring atoms on the aromatic ring are carbon atoms. Carbocyclic groups include phenyl and naphthyl groups which may be optionally substituted with 1 to 5 substituents such as alkyl, alkoxy, amino, amido, cyano, carboxylate ester, hydroxyl, halogen, acyl, nitro.

The term "aralkyl" refers to an alkyl group substituted with an aryl group. Suitable aralkyl groups include benzyl, and the like, and may be optionally substituted.

The term "aroyl" refers to —C(O)R where R is aryl group.

The term "alkoxycarbonyl" refers to —C(O)OR wherein R is alkyl, akenyl, alkynyl, aryl, aralkyl.

The term "acyl" refers to the alkanoyl group —C(O)R where R is alkyl, alkenyl, alkynyl, aryl, aralkyl.

The term "acyloxy" refers to the alkanoyl group —OC(O)R where R is alkyl, alkenyl, alkynyl, aryl, aralkyl.

The term "aminoalkyl" refers to alkyl which is substituted with amino groups.

The term "arylamino" refers to amino groups substituted with one or more aryl radicals.

The term "aminocarbonyl" refers to —C(O)$NRR_1$ wherein R and $R_1$ are independently selected from hydrogen, alkyl, akenyl, alkynyl, aryl, aralkyl.

The azidoalkyl refers to alkyl R which is substituted with azido —$N_3$.

The term "amino" refers to —$NRR_1$ where R and $R_1$ are independently hydrogen, lower alkyl or are joined together to give a 5 or 6-membered ring such as pyrrolidine or piperidine rings which are optionally substituted.

The term "alkylamino" includes amino groups substituted with one or more alkyl groups.

The term "dialkylamino" refers to —$NRR_1$ R and $R_1$ are independently lower alkyl groups or together form the rest of ring such as morpholino. Suitable dialkylamino groups include dimethylamino, diethylamino and morpholino. The term "morpholinoalkyl" refers to alkyl R substituted with morpholine group.

The term "isocyanoalkyl" refers to alkyl R that is substituted with isocyano group —NCO.

The term "isothiocyanoalkyl" refers to alkyl R that is substituted with isothiocyano group —NCS.

The term "isocyanoalkenyl" refers to alkenyl R that is substituted with isocyano group —NCO.

The term "isothiocyanoalkenyl" refers to alkenyl R that is substituted with isothiocyano group —NCS.

The term "isocyanoalkynyl" refers to alkynyl R that is substituted with isocyano group —NCO.

The term "isothiocyanoalkynyl" refers to alkynyl R that is substituted with isothiocyano group —NCS.

The term "alkanoylamino" refers to —NRC(O)$OR_1$ where R and $R_1$ are independently hydrogen, lower alkyl, akenyl, alkynyl, aryl, aralkyl.

The term "formylalkyl" refers to alkyl R substituted with —CHO.

The term "optionally substituted" or "substituted" refers to groups substituted by one to five substituents, indepently selected from lower alkyl (acyclic or cyclic), aryl (carboaryl or heteroaryl) alkenyl, alkynyl, alkoxy, halo, haloalkyl (including trihaloalkyl, such as trifluoromeyl), amino, mercapto, alkylthio, alkylsulfinyl, alkylsulfonyl, nitro, alkanoyl, alkanoyloxy, alkanoyloxyalkanoyl, alkoxycarboxy, (—COOR, where R is lower alkyl), aminocarbonyl (—CONR$R_1$, where R and $R_1$ are indepently lower alkyl), formyl, carboxyl, hydroxyl, cyano, azido, keto, and cyclic ketals thereof, alkanoylamido, heteroaryloxy, and heterocarbocyclicoxy.

The term "lower" refers herein in connection with organic radicals or compounds defines such as one up to and including ten, preferably up to and including six, and more preferably one to four carbon atoms. Such groups may be straight chain, branched chain, or cyclic.

The term "heterocyclic" refers to carbon containing radicals having three, four, five, six, or seven membered rings and one, two, three, or four O, N, P, or S heteroatoms, e.g., thiazolidine, tetrahydrofuran, 1,4-dioxane, 1,3,5-trioxane, pyrrolidine, pyridyl, piperidine, quinuclidine, dithiane, tetrahydropyran, and morpholine or fused analogs containing any of the above.

The term "heteroaryl" refers to carbon containing 5-14 membered cyclic unsaturated radicals containing one, two, three, or four O, N, P, or S atoms and having 6, 10 or 14π electrons delocalized in one or more than one rings, e.g., pyridine, oxazole, indole, purine, pyrimidine, imidazole, benzimidazole, indazole, 2H-1,2-4-triazole, 1,2,3-triazole, 2H-1,2,3,4-tetrazole, 1H-1,2,3,4-triazolebenztriazole, 1,2,3-triazolo[4,5-b]pyridine, thiazole, isoxazole, pyrazole, quinoline, cytosine, thymine, uracil, adenine, guanine, pyrazine, picoline, picolinic acid, furoic acid, furfural, furyl alcohol, carbazole, isoquinoline, pyrrole, thiophene, furan, phenoxazine, and phenothiazine, each of which may be optionally substituted.

The term "pharmaceutically acceptable esters, amides, or salts" refers to esters, amides, or salts of FIG. 1 derived from the combination of a compound of this invention and an organic or inorganic acid.

The term "nicotine-related agent" refers to nicotine-related alkaloids, nicotine metabolites, nicotine analogues, and nicotine derivatives, as further described herein.

The term "inhibit" means to reduce by a measurable amount, or to prevent entirely.

"Treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein.

"Preventing," "prophylaxis," or "prevention" of a disease or disorder means prevention of the occurrence or onset of a disease or disorder or some or all of its symptoms.

The term "subject" as used herein means any mammalian patient to which the compositions of the present invention may be administered according to the methods described herein. Subjects specifically intended for treatment or prophylaxis using the methods of the present invention include humans.

The term "therapeutically effective regime" means that a pharmaceutical composition or combination thereof is administered in sufficient amount and frequency and by an appropriate route to at least detectably prevent, delay, inhibit, or reverse development of at least one symptom or biochemical marker of a nicotine-related disorder. In certain embodiments, the "therapeutically effective regime" predisposes a subject to ingest lower amounts of nicotine and/or inhibits mutagenic activation of N-nitrosamines to in turn decrease the risk of developing cancer.

The term "therapeutically effective amount" refers to an amount of an nicotine-related agent, or a combination of a nicotine-related agent with other agent(s), is present to achieve a desired result, e.g., preventing, delaying, inhibiting, or reversing a symptom or biochemical marker of a nicotine-related disorder when administered in an appropriate regime.

DESCRIPTION OF THE EMBODIMENTS

The present disclosure relates to methods of reducing the risk of cancer as well as treating nicotine addiction and other CNS diseases by inhibiting the metabolism of tobacco-specific N-nitrosamines and nicotine and/or of modulating the binding and or reuptake of neurotransmitters. More specifically, the present disclosure relates to the prophylaxis of cancer (e.g., lung cancer) and smoking and tobacco addiction through the use of small molecule nicotine-related agents and synthetic derivatives thereof. These compounds are also useful in the treatment of other CNS diseases, including, e.g., neurodegenerative diseases and psychiatric disorders (e.g., drug abuse, alcoholism, anxiety, attention deficit disorder (ADD), and bipolar disorder).

In one aspect, disclosed herein are inhibitors of cytochrome P-450 2A6 (CYP2A6). CYP2A6 inhibitors are useful for, e.g., reducing nicotine ingestion (e.g., smoking, chewing tobacco or snuff) and addiction. Inhibition of CYP2A6 using a compound as described herein reduces nicotine metabolism in a subject in whom nicotine is present, thereby increasing blood levels of nicotine and predisposing the subject to ingest lower amounts of nicotine. CYP2A6 inhibitors as described herein are also useful for decreasing metabolism of other products, including, for example, promutagens that are activated by CYP2A6 to mutagens. For example, inhibition of CYP2A6 is useful for preventing mutagenic activation of the carcinogenic, tobacco-specific promutagen 4-(methylnitrosamino)-1-(3-pyridyl)-1-butanone (NNK), thereby decreasing the risk of developing cancer.

In preferred embodiments, an agent of the present invention is a selective or dual inhibitor of CYP2A6 and/or CYP2A13. CYP2A13, another cytochrome P-450 monooxygenase, shows predominant expression in the respiratory tract (see, e.g., Su et al., *Cancer Res.* 60:5074-5079, 2000). CYP2A13 has been shown to present a higher activity in the metabolism of several nitrosamines than CYP2A6 when expressed in a heterologous system. Accordingly, dual inhibitors of CYP2A6 and CYP2A13 have enhanced therapeutic and prophylactic effects against disorders associated with, e.g., nicotine and tobacco ingestion. In addition, a selective inhibitor of CYP2A13 has enhanced therapeutic and prophylactic effects against disorders associated with, e.g., nicotine and tobacco ingestion.

The effects of nicotine on mood and tobacco seeking behavior are mediated by acetylcholinergic receptors in the central nervous system which respond selectively to nicotine. Accordingly, in other preferred embodiments, an agent of the present invention is a dual CYP2A6 and/or CYP2A13 inhibitor and nicotinic acetylcholine receptor (nAChR) binding agent. In certain variations, the compound selectively modulates the α/β. Agents that selectively modulate the nAChR (e.g., blunt) nicotinic central nervous system (CNS) activity and may also be used for treatment of nicotine addiction to reduce the use and exposure to the harmful ingredients in tobacco products and their smoke.

In yet other variations of the present invention, selective modulation of α7 nAChRs are useful, for example, for various CNS associated applications. For example, selective modulation of nAChRs is useful for enhancing cognition or for inducing a neuroprotective effect in a subject in need thereof. In addition, modulation of nAChRs are useful for treatment or prophylaxis of various CNS-associated disorders and diseases, including, for example, neurodegenerative diseases (e.g., Alzheimer's Disease, Parkinson's Disease, and the like) as well as various psychiatric disorders (e.g., anxiety, attention deficit disorder (ADD), bipolar disorder, drug abuse and the like). In particular embodiments, the nAChR is the α7 nAChR (e.g., for treatment of neurodegenerative disease such as Alzheimer's Disease or Parkinson's Disease). Depending on the application, the compound that selectively modulate nAChRs to blunt the activity thereof as an agonist or an antagonist of the nAChR or by some indirect mechanism including allosteric interactions with the receptor or other receptors or biological factors.

CYP2A6/CYP2A13 Inhibitors and nAChR Binding Agents

In one embodiment, disclosed herein are compounds of Formula I:

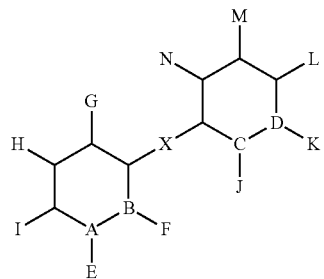

(I)

or pharmaceutically acceptable salts, esters, amides, and other forms or prodrugs, thereof, wherein A, B, C, D, E, F, G, H, I, J, K, L, M, N and X are further defined. In the foregoing, the stereochemistry is designated and isomers at the various centers of chirality are included.

The general structure is shown in Formula I wherein:

A and B, along with the ring carbon atoms to which they are attached, and C and D, along with the ring carbon atoms to which they are attached, independently form a 5- or 6-member, saturated or unsaturated, heterocyclo or carbocyclic, ring system, A, B, C, D is each independently selected from the group consisting of carbon, nitrogen, oxygen and sulfur, or is absent; and A, B, C, and D is each independently and optionally substituted with hydrido, acyl, halo, lower acyl, lower haloalkyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl, aryl, lower aralkylthio, lower alkylsulfinyl, lower alkylsulfonyl, aminosulfonyl, lower N-arylaminosulfonyl, lower arylsulfonyl, or lower N-alkyl-N-arylaminosulfonyl; wherein aryl is selected from phenyl, biphenyl, naphthyl, and 5- or 6-membered heteroaryl and is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy; and wherein the acyl group is optionally substituted with a substituent selected from hydrido, alkyl, halo, and alkoxy.

In one embodiment of the compound of Formula I, A is optionally substituted with hydrido, acyl, halo, lower acyl, lower haloalkyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

In another embodiment, the substituents A and B taken together with the other carbon atoms of the ring of which they are a part, and C and D taken together with the other carbon atoms of the ring of which they are a part, each independently form a ring system selected from the group consisting of pyranyl, furyl, tetrahydrofuryl, tetrahydrothienyl, thienyl, oxazolyl, pyrolyl, thiazolyl, imidazolyl, isthiazolyl, isoxazoly, pyrazolyl, cyclopentyl, phenyl, and pyridyl.

E, F, G, H, I, J, K, L, M, and N are each independently selected from the group consisting of aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, naphthyl, and 5- or 6-membered heteroaryl, wherein the aryl or heteroaryl is optionally substituted. In addition, two adjacent groups are optionally joined together to form a fused carbocyclic or heterocyclic ring system. For example, E and F may be part of a ring that is fused to a 5- or 6-membered ring system in Formula I.

In one embodiment, each of the 5- or 6-membered ring system having the substituents A and B or C and D forms a heterocyclic ring system selected from the group comprising pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine, 4-phenylpiperidine, 1-(fluorophenyl)piperazine, 1,3,5-hexa-hydrotriazine, morpholine, phenylmorpholine, thiomorpholine, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —$OR_4$, —$R_5$, —$OC(O)R_6$, $OC(O)NR_7R_8$, —$C(O)R_9$, —CN, —$NR_{10}R_{11}$, —$SR_{12}$, —$S(O)R_{11}$, —$S(O)_2R_{14}$, —$C(O)OR_{15}$, —$S(O)_2NR_{16}R_{17}$; —$R_{18}NR_{19}R_{20}$ wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals.

In another embodiment, the substituent X is absent or is selected from the group comprising of aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, naphthyl, and 5- or 6-membered heteroaryl, wherein aryl or heteroaryl is optionally substituted. In addition, two adjacent groups are optionally joined together to form a fused carbocyclic or heterocyclic ring system.

In another embodiment, disclosed herein are compounds of Formula II:

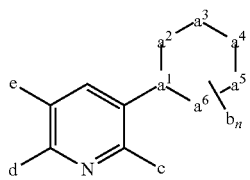

(II)

wherein $a^1$, $a^2$, $a^3$, $a^4$, $a^5$ and $a^6$ are each independently selected from the group consisting of carbon, nitrogen, oxygen and sulfur, or is absent, each of which is substituted with enough hydrogen atoms to complete its octet of electrons.

In one embodiment, $a^1$, $a^2$, $a^3$, $a^4$, $a^5$ and $a^6$ are part of a 5- or 6-membered, unsaturated or partially unsaturated ring system. In another embodiment, $a^1$ and $a^2$ are carbon and $a^3$, $a^4$, $a^5$ and $a^6$ are absent.

In some embodiments, each "b" is independently selected from the group consisting of hydrogen, methyl, lower alkyl, aminomethyl, N-methylaminomethyl, benzyl, oximino, amino, nitro, ethyl, formyl, bromomethyl, heteroarylaminomethyl, heteroaryl, 3-(3-methylthienyl)pyridyl, 2-(3-methyl)thienyl, 3-thienyl, $CH_3(C=O)-$, N,N-dimethylaminomethyl, aminopropyl, hydroxymethyl, pyridyl and oxo; and n is an integer from 0 to 10, for example, 0, 1, 2, 3, 4, 5, 6, 7, 8, 9, and 10. Alternatively, any two substituents "b" adjacent to each other on the 5- or 6-membered ring may be taken together with the atoms to which they are attached to form a 5- or 6-membered aryl or heteroaryl ring system.

c is hydrogen or amino.

d is selected from the group consisting of hydrogen, fluoro, methoxy, amino and chloro.

e is a substituent selected from the group consisting of hydrogen, methyl, 2-(3-methylthienyl), $CH_3O(C=O)-$, bromo, ethynyl, 3-thienyl and hydroxymethyl.

In one embodiment of Formula II, $a^1$, $a^2$, $a^3$, $a^4$, $a^5$ and $a^6$ form a 5- or 6-member ring system, or a bicyclic ring system, selected from the group consisting of:

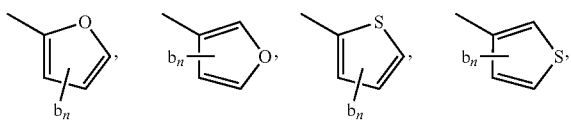

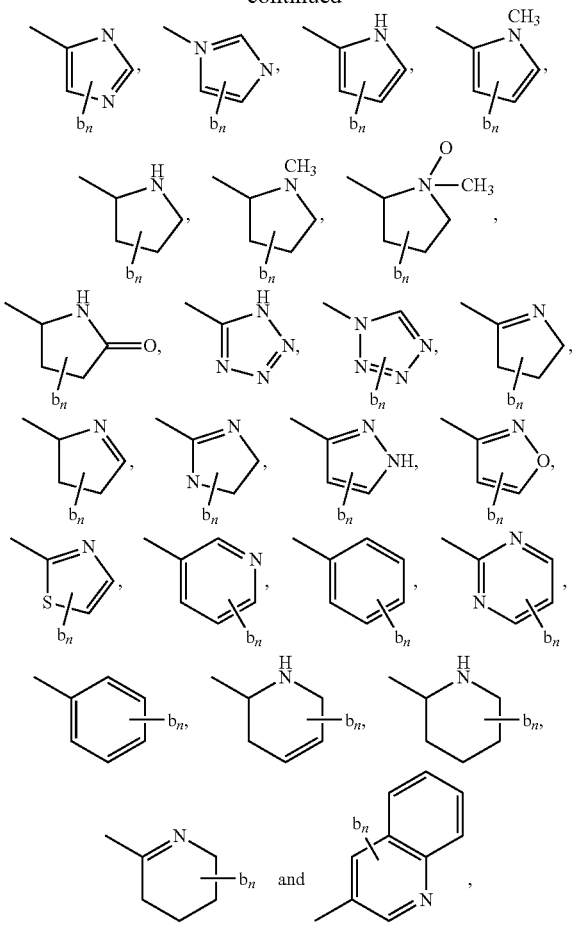

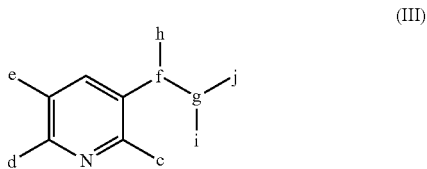

wherein b and n are as defined above.

In another embodiment, the compound of Formula II is a compound of Formula III:

(III)

wherein
  f and g are each carbon or nitrogen atom; and wherein f and g are connected to each other by a single, double or triple bond;
  h and i are each independently hydrogen, lower alkyl group, or is absent; and wherein h and i together with the atoms to which they attached may optionally be combined to form a 3- to 5-membered ring;
  j is selected from the group consisting of aminomethyl, N-methylaminomethyl, amino, 2-(3-methyl)thienyl, 3-thienyl, N,N-dimethylaminomethyl, heteroaryl and 3-(3-methylthienyl)pyridyl;
  c is hydrogen or amino;
  d is selected from the group consisting of hydrogen, fluoro, methoxy, amino and chloro; and e is a substituent selected from the group consisting of hydrogen, methyl, 2-(3-methylthienyl), $CH_3O(C=O)$—, bromo, ethynyl, 3-thienyl and hydroxymethyl.

In yet another embodiment, disclosed herein are methods of decreasing cravings for smoking cigarettes in an animal or human comprising administering a compound of claim 1 by itself, or in combination with other agents or biologically or chemically tenable material.

In another embodiment, disclosed herein are methods of selectively inhibiting CYP2A6 and/or 2A13 by administering a compound of Formula I alone or in combination with other agents or biologically or chemically tenable material. In some embodiments, the inhibition of CYP2A6 and/or 2A13 inhibits the mutagenic activation of promutagens such as the tobacco-specific nitrosamine, 4-(methylnitrosamino)-1-(3-pyridyl)-1-butanone (NNK), by CYP2A6 and/or 2A13 and in turn, is used as a chemopreventive agent against NNK-induction of lung tumorigenesis. In one embodiment, the compound of Formula I, is 1-phenethyl-2-imidazol-1-yl.

In another embodiment, disclosed herein are methods of preventing or treating neurodegenerative diseases selected from the group consisting of Alzheimer's and Parkinson's disease, by administering a compound having a structure of I alone or in combination with other agents or biologically or chemically tenable material. In one embodiment, the compound of Formula I is 1-Phenethyl-2-imidazol-1-yl. In one embodiment, the compound used in the aforementioned method, having Formula I, is N-(cyclohexylmethyl)imidazole In another embodiment, disclosed herein are methods of enhancing cognition by selective stimulation or antagonism of biological receptors, by administering a compound of Formula I alone or in combination with other agents or biologically or chemically tenable material. In one embodiment, the compound of Formula I is N-(4-pyridylethyl)imidazole or 1-phenethyl-2-imidazol-1-yl.

In another embodiment, disclosed herein are methods of reducing alcoholism or anxiety in an animal or human, by administering a compound of Formula I alone or in combination with other agents or biologically or chemically tenable material. In one embodiment, the compound of Formula I is 1-phenethyl-2-imidazol-1-yl.

In another embodiment, disclosed herein are methods of providing neuroprotective activity with little or no side effects by the selective stimulation/inhibition of biological receptors in an animal or human by administering a compound of Formula I alone, or in combination with other agents or biologically or chemically tenable material. In one embodiment, the compound of Formula I is 1-phenethyl-2-imidazol-1-yl.

In another embodiment, disclosed herein are methods of improving bipolar disorder by administering a compound of Formula I alone, or in combination with other agents or biologically or chemically tenable material. In one embodiment, the compound of Formula I is 1-phenethyl-2-imidazol-1-yl.

Pharmaceutical Compositions and Methods of Administration

The nicotine-related agents disclosed herein are useful for the treatment of diseases and disorders associated with nicotine ingestion and metabolism. For example, the compounds disclosed herein are useful for the treatment of nicotine addiction (e.g., smoking cessation and reduction) as well as for the prophylaxis of lung cell tumorigenesis caused by, e.g., N-nitrosamines.

The disclosed agents are also useful for the treatment of CNS diseases and disorders amenable to treatment by selective modulation (e.g., stimulation or inhibition) of biological receptors (including nAChRs). Such diseases include, for example, neurodegenerative diseases (e.g., Alzheimer's Disease or Parkinson's Disease) and psychiatric disorders such as, e.g., anxiety, attention deficit disorder (ADD), drug abuse, alcoholism and bipolar disorder. The compounds disclosed herein are also useful for other CNS-related therapeutic applications, including, for example, inducing neuroprotective activity in a subject in need thereof (e.g., for treatment or prophylaxis of conditions associated with neurotoxicity), as well as enhancing cognition through selective stimulation of receptors.

Accordingly, disclosed herein are pharmaceutical compositions and methods for the treatment of nicotine-related disorders. The nicotine-related agents of the present invention can be delivered or administered to a mammal, e.g., human subject, alone, in the form of a pharmaceutically acceptable salt or hydrolysable precursor thereof, or in the form of a pharmaceutical composition wherein the compound is mixed with suitable carriers or excipient(s) in a therapeutically effective amount. In a preferred embodiment, for treating nicotine addition in a subject and when administered in an appropriate therapeutically effective regime, a sufficient amount of the nicotine-related agent is present to decrease nicotine metabolism so as to predispose the subject to ingest lower amounts of nicotine.

The nicotine-related and other active agents that are used in the methods disclosed herein can be administered as pharmaceutical compositions comprising the nicotine-related alkaloid, nicotine metabolite, or nicotine analogue together with a variety of other pharmaceutically acceptable components. Pharmaceutical compositions can be in the form of solids (such as, e.g., powders, granules, dragees, tablets, or pills), semi-solids (such as, e.g., gels, slurries, or ointments), liquids, or gases (such as, e.g., aerosols or inhalants).

Suitable formulations for use in the disclosed methods are found in, for example, *Remington's Pharmaceutical Sciences* (Mack Publishing Company, Philadelphia, Pa., 17th ed. 1985) and Langer, *Science* 249:1527-1533, 1990. The pharmaceutical compositions described herein can be manufactured in a conventional manner, e.g., mixing, dissolving, granulating, dragee-making, levigating, emulsifying, encapsulating, entrapping, or lyophilizing processes.

In preparing the formulations disclosed herein, pharmaceutically recognized equivalents of each of the compounds can be alternatively used. These pharmaceutically recognized equivalents can be pharmaceutically acceptable esters, amides, or salts or pharmaceutically acceptable acid addition salts.

A pharmaceutically acceptable salt is a non-toxic metal, alkaline earth metal, or an ammonium salt commonly used in the pharmaceutical industry including, for example, a sodium, potassium, lithium, calcium, magnesium, barium, ammonium, and protamine zinc salt, which is prepared by methods well-known in the art. The term also includes a non-toxic acid addition salt, which is generally prepared by treating the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt that retains the biological effectiveness and properties of the free bases and that is not biologically or otherwise undesirable, formed with inorganic acids such as, e.g., hydrochloric acid, hydrobromic acid, sulfuric acid, nitric acid, phosphoric acid, and the like, and organic acids such as, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid, and the like (see, e.g., Bundgaard ed., *Design of Prodrugs* (Elsevier Science Publishers, Amsterdam 1985)).

The nicotine-related agents can be formulated with common excipients, diluents or carriers, and compressed into tablets, for formulated as elixirs or solutions for convenient oral administration. The nicotine-related agents can also be formulated as sustained release dosage forms and the like.

In order to exert the desired therapeutic effects associated with binding of the biological receptor, the nicotine related agents of the present invention must reach brain cells and brain tissue, requiring their passage from the blood to the brain by crossing the blood brain barrier, comprising the microcapillary membranes of the cerebrovascular endothelium. The present invention provides methods for administering a therapeutically effective dosage regime of the nicotine-related agent to a peripheral tissue in a patient (i.e., tissues other than central nervous system tissues). This can be achieved in various ways, including oral, buccal, rectal, nasal, parenteral, intraperitoneal, intradermal, transdermal, intratracheal, and intramuscular administration. Moreover, the nicotine-related agents can be administered in a local rather than systemic manner, in a depot or sustained release formulation. In addition, the nicotine related agents can be administered in a vesicle, in particular a liposome (see, e.g., Langer, supra; Treat et al., In *Liposomes in the Therapy of Infectious Disease and Cancer*, Lopez-Berestein and Fidler eds., Liss, New York, pp. 353-365, 1989).

For injection, the nicotine-related agents of the present invention can be formulated into preparations by dissolving, suspending, or emulsifying them in an aqueous or nonaqueous solvent such as, e.g., vegetable or other similar oils, synthetic aliphatic acid glycerides, esters of higher aliphatic acids, or propylene glycol; and, if desired, with conventional additives such as, e.g., solubilizers, isotonic agents, suspending agents, emulsifying agents, stabilizers, and preservatives. Preferably, for injection, the compounds of the present invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the nicotine-related agent can be formulated readily by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Particularly suitable excipients include fillers such as, for example, sugars (e.g., lactose, sucrose, mannitol, or sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as, e.g., sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, titanium dioxide, lacquer solutions, and/or suitable organic solvents or solvent mixtures. Dyestuffs or pigments can be added to the tablets or dragee coatings for identification or to characterize different combinations of active compound doses.

Pharmaceutical preparations that can be used orally include, for example, push-fit capsules made of gelatin, as well as soft, sealed capsules made of gelatin and a plasticizer, such as, e.g., glycerol or sorbitol. The push-fit capsules can contain the active ingredients in admixture with filler such as, for example, lactose, binders (e.g., starches), and/or lubricants (e.g., talc or magnesium stearate) and, optionally, stabilizers. In soft capsules, the active compounds can be dissolved or suspended in suitable liquids, such as, e.g., fatty oils, liquid paraffin, or liquid polyethylene glycol.

For buccal administration, the compositions can take the form of tablets or lozenges formulated in a conventional manner.

For administration by inhalation, the compounds for use in accordance with the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by, for example, providing a valve to deliver a metered amount. Capsules and cartridges of, e.g., gelatin for use in an inhaler or insufflator can be formulated containing a powder mix of the compound and a suitable powder base such as, for example, lactose or starch.

Nicotine-related agents disclosed herein can be formulated for parenteral administration by injection, e.g., by bolus injection or continuous infusion. Formulations for injection can be presented in unit dosage form, e.g., in ampules or in multidose containers, with an added preservative. The compositions can take such forms as, e.g., suspensions, solutions, or emulsions in oil-based or aqueous vehicles, and can contain formulator agents such as, for example, suspending, stabilizing, and/or dispersing agents.

Pharmaceutical formulations for parenteral administration include aqueous solutions of the active compounds in water-soluble form. Alternatively, suspensions of the active compounds can be prepared as appropriate oily injection suspensions. Suitable lipophilic solvents or vehicles include fatty oils (e.g., sesame oil), synthetic fatty acid esters (e.g., ethyl oleate or triglycerides), or liposomes. Aqueous injection suspensions can contain substances that increase the viscosity of the suspension, such as, for example, sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

Nicotine-related agents can also be formulated in rectal compositions such as suppositories or retention enemas, e.g., containing conventional suppository bases such as, for example, cocoa butter, carbowaxes, polyethylene glycols, or other glycerides, all of which melt at body temperature, yet are solidified at room temperature.

In addition to the formulations described previously, the compounds can also be formulated as a depot preparation. Such long-acting formulations can be administered by implantation (for example, subcutaneously or intramuscularly) or by intramuscular injection. Accordingly, for example, the compounds can be formulated with suitable polymeric or hydrophobic materials (e.g., as an emulsion in an acceptable oil) or ion exchange resins, or as sparingly soluble derivatives (e.g., a sparingly soluble salt).

Alternatively, other delivery systems for hydrophobic pharmaceutical compounds can be employed. Liposomes and emulsions are well-known examples of delivery vehicles or carriers for hydrophobic drugs. In some methods, long-circulating, e.g., stealth, liposomes can be employed. Such liposomes are generally described in U.S. Pat. No. 5,013,556 to Woodle et al.

The compounds disclosed herein can also be administered by controlled release means and/or delivery devices. In certain variations, a pump is used (see, e.g., Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989). In other embodiments, polymeric materials are used (see, e.g., *Medical Applications of Controlled Release*, Langer and Wise eds., CRC Pres., Boca Raton, Fla., 1974; *Controlled Drug Bioavailability, Drug Product Design and Performance*, Smolen and Bull eds., Wiley, New York, 1984; Ranger and Peppas, *J. Macromol. Sci. Rev. Macromol. Chem.* 23:61, 1983; see also Levy et al., *Science* 228:190, 1985; During et al., *Ann. Neurol.* 25:351, 1989; Howard et al., *J. Neurosurg.* 71:105, 1989). Controlled release means and delivery devices are also described in, e.g., U.S. Pat. Nos. 3,845,770; 3,916,899; 3,536,809; 3,598,123; and 4,008,719.

Certain organic solvents such as, e.g., dimethylsulfoxide (DMSO) also can be employed, although usually at the cost of greater toxicity. Additionally, the compounds can be delivered using a sustained-release system such as, for example, semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

For treatment or prophylaxis of diseases or disorders associated with nicotine ingestion (e.g., nicotine addiction or lung cancer), compounds of the present invention may also be administered by incorporating the agent into a nicotine-containing product (for example, a tobacco product such as, e.g., a cigarette). For example, in certain embodiments, a compound of the present invention is sprayed or otherwise applied onto the nicotine-containing product prior to ingestion.

Pharmaceutical compositions suitable for use in accordance with the present invention include compositions wherein the active ingredients are contained in a therapeutically effective amount. The therapeutically effective amounts for the methods of the present invention can depend on a variety of factors, including, e.g., age, body weight, general health, sex, diet, time and manner of administration, rate of excretion, drug combination, the judgment of the treating physician, and the severity of the particular affliction being treated. The amount of active agent will also depend upon the specific activity of the nicotine-related agent and whether that agent is co-administered with any other therapeutic or prophylactic ingredients.

Typically, a subject treated in accordance with the methods provided herein has been diagnosed with a disease or disorder amenable to treatment using a compound of the present invention; has been identified as at risk of a disease or disorder amenable to prophylaxis using the compound; or has otherwise been identified as a subject that will obtain a physiological benefit using the compound (e.g., cognition enhancement). In certain variations, the subject has not been diagnosed with another disease or disorder amenable to treatment using the compounds of the present invention. Further, in some embodiments, the subject is monitored during treatment for one or more symptoms associated with the disease or disorder.

EXAMPLES

The following examples are offered to illustrate, but not to limit, the claimed invention.

Example 1

Chemical Synthesis of Nicotine Analogs

General procedure for the synthesis of 1-alky and 1-benzylimidazoles. Into a 20 mL vial was placed the alkyl or benzyl halide (1.0 equiv.) and imidazole (3.0 equiv.). The neat mixture was heated to 90° C. for 3 h with stifling at which time the reactants melted. After three hours the reaction was cooled to room temperature and the resulting residue was partitioned between 5 M NaOH and $CH_2Cl_2$ (10 mL each). The organic portion was removed and concentrated in vacuo. The target compounds were fully characterized spectrally and subjected to biological evaluation. Purity was determined to be >95% by HPLC analysis of the compounds.

N-(4-Chlorobenzyl)imidazole (Compound 3)

The title compound was purified by silica gel chromatography using 10% MeOH in $CH_2Cl_2$ (53% yield). $^1$H NMR (300 MHz, $CDCl_3$) δ 4.9 (s, 2H), 6.72 (s, 1H), 6.89 (m, 3H), 7.11 (m, 2H), 7.36 (s, 1H); $^{13}$C NMR (75.43 MHz, $CDCl_3$) δ 50.06, 119.03, 128.41, 129.02, 129.91, 134.21, 137.23. LRMS (ESI) m/z calcd for $C_{10}H_9ClN_2$ [M+H]$^+$ 192. found 192.

N-(3-Pyridylmethyl)imidazole (Compound 7)

The title compound was purified by silica gel chromatography using 10% MeOH in $CH_2Cl_2$ (28% yield). $^1$H NMR (300 MHz, $CDCl_3$) δ 5.07 (s, 2H), 6.82 (s, 1H), 6.98 (s, 1H), 7.2 (m, 1H), 7.36 (m, 1H), 7.48 (s, 1H), 8.42 (m, 1H); $^{13}$C NMR (75.43 MHz, $CDCl_3$) δ 48.29, 118.95, 123.76, 130.19, 131.68, 134.71, 137.17, 148.48, 149.68; LRMS (ESI) m/z calcd for $C_9H_9N_3$ [M+H]$^+$ 159. found 159.

N-(4-Pyridylethyl)imidazole (Compound 9)

The title compound was purified by silica gel chromatography using 5% MeOH in $CH_2Cl_2$ (77% yield). $^1$H NMR (300 MHz $CDCl_3$); δ 3.04 (2H, t, J=6.8), 4.20 (2H, t, J=6.8), 6.81 (1H, s), 6.96 (2H, d, J=6.1), 7.03 (1H, s), 7.34 (1H, s), 8.5 (2H, d, J=6.1); LRMS (ESI) m/z calcd for $C_{10}H_{11}N_3$ [M+H]$^+$ 174. found 174.

N-(Cyclohexylmethyl)imidazole (Compound 10)

The title compound was purified by silica gel chromatography using 10% MeOH in $CHCl_3$ (62% yield). $^1$H NMR (300 MHz, $CDCl_3$) δ 0.75 (m, 2H), 1.00 (m, 3H), 1.47 (m, 6H), 3.55 (d, 2H, J=Hz), 6.89 (s, 1H), 6.83 (s, 1H), 7.23 (s, 1H); $^{13}$C NMR (75.43 MHz, $CDCl_3$) δ 25.63, 26.18, 30.59, 39.36, 53.48, 119.21, 128.98, 137.34; LRMS (ESI) m/z calcd for $C_{10}H_{16}N_2$ [M+H]$^+$ 164. found 164.

1-Phenethyl-2-imidazol-1-yl (Compound II)

The title compound was purified by silica gel chromatography using 10% MeOH in $CH_2Cl_2$ (38% yield). $^1$H NMR (300 MHz, $CDCl_3$) δ 2.94 (t, 2H, J=Hz), 4.06 (t, 2H, J=Hz), 6.75 (s, 1H), 6.97 (m, 3H), 7.13-7.25 (m, 4H); $^{13}$C NMR (75.43 MHz, $CDCl_3$) δ 37.88, 48.54, 118.65, 126.85, 128.44, 128.62, 129.19, 136.91, 137.27; LRMS (ESI) m/z calcd for $C_{11}H_{12}N_2$ [M+H]$^+$ 172. found 172.

Example 2

Nicotine Analogs as Inhibitors of CYP2A6 Mediated Coumarin 7-Hydroxylation

The inhibition of human CYP2A6-mediated 7-hydroxy coumarin formation was evaluated in the presence of select test compounds in a standard assay (Greenlee et al., *J Pharmacol Exp Ther*, 1978). Our first studies were with highly purified human CYP2A6 that provided a convenient and relatively high-throughput measure of CYP2A6 inhibition. Full dose-response $IC_{50}$ values (nine concentrations) were determined (Table 1).

TABLE 1

Inhibition of human CYP2A6 and rat CYP2B6 in the presence of substituted heteroaromatic compounds and physicochemical properties of compounds 1-11.

| Compd | hCYP2A6 $IC_{50}$ (µM) | hCYP2B6 $IC_{50}$ (µM) | rCYP2B1 % inhibition[a] | rCYP2B1 % inhibition[b] | tPSA[c] | CLogP[d] |
|---|---|---|---|---|---|---|
| 1 | 0.6 | 66.4 | ND[e] | 53.8 | 62.8 | 0 |
| 2 | 0.8 | 67.4 | ND | 55.3 | 59.9 | −0.2 |
| 3 | 0.16 | 12 | ND | 35.5 | 15.6 | 2.5 |
| 4 | 0.16 | 52.2 | ND | 42.7 | 38.4 | 1.4 |
| 5 | 0.2 | 3.9 | ND | 47.9 | 12.4 | 2.6 |
| 6 | 0.2 | 191 | ND | 46.6 | 47.6 | 0.9 |
| 7 | >200 | ND | ND | 43.3 | 27.9 | 0.3 |
| 8 | 800 | 103 | NA | NA | 36.7 | 0.7 |
| 9 | NA[f] | NA | ND | 53.5 | 27.9 | 0.6 |
| 10 | 170 | 11 | ND | 56.9 | 15.6 | 2.6 |
| 11 | 618 | >20 | ND | 67.7 | 15.6 | 2.1 |

[a]Inhibitor present at 25 µM;
[b]Inhibitor present at 100 µM;
[c]tPSA, Total Polar Service Area;
[d]CLogP, Log of the Partition Ratio;
[e]ND, no detectable inhibition,
[f]NA, not available.

Example 3

CYP Inhibition Assay

To gain insight into the selectivity of the synthetic compounds for inhibition of other CYPs, we examined the major CYPs present in human liver. Prior to these studies we showed that the nicotine analogs were quite metabolically stable in the presence of mouse or rat or human liver microsomes (i.e., $T_{1/2}$>60 mins). That the nicotine analogs showed low or no inhibitory activity against other CYPs suggests that the inhibitors examined selectively inhibited CYP2A6. A typical incubation mixture (final volume 0.25 mL) contained 50 mM Tris or KPhos buffer (pH 7.5), 0.5 mM NADP$^+$, 2.0 mM G6P, 1 U of G6P dehydrogenase and 0.6 mg DETAPAC and the inhibitor was added last to minimize interaction with the protein. After mixing on ice, the reaction was initiated by the addition of substrate and incubated at 37° C. with shaking in air. Organic extracts were analyzed by fluorescence (for fluorometric substrates) or injected onto a Hitachi L-7100 system equipped with a Hitachi L-7400 UV detector. Separations were done with an Altex Ultrasphere ODS (4.6 mm×250 mm, 5 µm) column and analytes were eluted with an isocratic solvent system consisting of water/acetonitrile/methanol (30:10:60, v/v/v) at a flow rate of 1.0 mL/min. Quantification of substrate and metabolite was determined from peak areas of the chromatogram and comparison with standard curves. $IC_{50}$ values were determined with GraphPad Prism and kinetic data was converted into $IC_{50}$ values. Each kinetic determination was reported as the mean±SD as described below. For each assay, the reaction was a linear function of time for 60 min and of protein concentration from 0.2 to 1 mg of protein per reaction well. To measure CYP2A6 activity, coumarin 7-hydroxylation was determined as described in Denton et al., supra. To measure CYP3A4 activity, testosterone 6-hydroxylation was determined as described in Denton et al., supra. To measure CYP2E1, CYP2B6, CYP2C9, CYP2C19 and CYP2D6 activity, isozyme specific vivid blue substrate O-dealkylation was determined via a modified PanVera Vivid Assay Protocol as described in Denton et al., supra.

TABLE 2

Percent Inhibition of CYP3A4, 2E1, 2C9, 2C19, or 2D6 by Alkyl- or Aryl-Imidazoles[a].

| Compound | CYP3A4 | CYP2E1 | CYP2C9 Percent Inhibition | CYP2C19 | CYP2D6 |
|---|---|---|---|---|---|
| 3 | 23 | 87 | 32 | 43 | 48 |
| 10 | 27 | 89 | 44 | 24 | 34 |
| 11 | 63 | 88 | 13 | 21 | 62 |

[a]10 µM concentration of alkyl or aryl imidazole used. Values are the mean of triplicate determinations.

Example 4

Inhibition of CYP2A6 by Compounds 8-11

In the presence of compounds 3-6 and 10, significant inhibition of human CYP 2A6 was observed (Tables 1 and 3). Compared to tranylcypromine, compounds 3-6 and 10 were more potent human CYP 2A6 inhibitors. The selectivity of human CYP 2A6 inhibition was examined by studying the effect of compounds 3, 10 and 11 on the selective functional activity of human CYP 3A4, 2E1, 2C9, 2C19, 2D6 and 2B6 at a concentration of 10 µM. As shown in Table 2, compounds 3, 10 and 11 showed some inhibition of human CYP 2E1. Compounds 3, 10 and 11 also inhibited human CYP 2B6 to a certain extent. However, a 16- to 125-fold greater concentration of compounds 3, 10 and 11 was required to achieve the same degree of inhibition of human CYP 2A6. The results indicated that compounds 3, 10 and 11 were relatively selective inhibitors of human CYP 2A6. However, even though compounds 3, 10 and 11 were selective inhibitors of human CYP 2A6, the degree of blockade of nicotine self-administration for these compounds did not exactly follow suit.

We examined the inhibition of rat CYP 2B1 by compounds I-7 and 9-11 because CYP 2B 1 is the prominent nicotine metabolizing enzyme in rat liver and largely responsible for nicotine clearance in rat. As shown in Table 1, compounds I-7 and 9-11 were ineffective at inhibiting rat CYP 2B 1. With the possible exception of compound II, all the compounds examined possessed an $IC_{50}$ value estimated to be greater than 100 µM. Accordingly, at the doses used in the in vivo experiments, compounds I-7 and 9-11 were unlikely to significantly inhibit rat CYP 2B 1 and decrease nicotine metabolism in the rat by this mechanism. To examine this point in greater detail, the influence of selected test compounds on nicotine clearance was studied in rats. There was no detectable decrease in area under the curve for formation of cotinine in rats (i.v. administration of 3.0 mg/kg nicotine 30 mins after a 25 mg/kg dose of nicotine analogs 4-6 and 8, i.p.). Accordingly, it was concluded that inhibition of CYP 2B1 in the rat is not the biological target. In addition, direct antagonism (or partial agonism) of mammalian nAChRs is not responsible for the biological effects of the test agents although these studies did not rule out indirect of allosteric mechanisms (Table 3). The nicotine analogs were also examined for their binding to the human dopamine transporter (hDAT). Compared to cocaine (as a positive control), no detectable binding (>10 μM) was observed for any of the nicotine analogs 1-11. Based on this observation it is unlikely that any of the compounds inhibit reuptake of the hDAT. Thus, inhibition of dopamine reuptake cannot explain the decrease in nicotine self-administration and the hDAT is apparently not a target for these compounds.

TABLE 3

Interaction of N-alkyl-substituted imidazoles with CYP2A6 and Nicotinic Acetylcholine Receptors

| Compd | Structure | CYP2A6 Inhibition IC$_{50}$, nM | [a]Nicotinic receptors μM |
|---|---|---|---|
|  | Tranylcypromine | 233 | — |
| 8 | 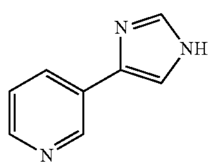 [SMILES: c1cncc(-c2c[nH]cn2)c1] | 800 | [b]NA |
| 9 | 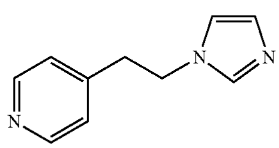 [SMILES: c1cc(CCn2ccnc2)ccn1] | NA | [c]ND |
| 10 | 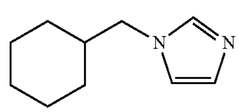 [SMILES: c1cn(CC2CCCCC2)cn1] | 170 | ND |
| 11 | 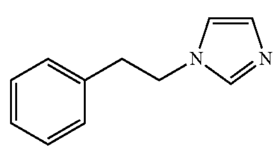 [SMILES: c1ccc(CCn2ccnc2)cc1] | 618 | ND |

[a]Mammalian α-7 and α4β2 nicotinic receptors;
[b]NA, Not available;
[c]ND, No detectable binding at 1 μM Example 5

Effect of Compounds I-7 on Nicotine Self-Administration

Male, Wistar rats trained in a paradigm of nicotine i.v. self-administration (IVSA) generally related to a modification of a previously published protocol (Watkins et al., *Pharmacol Biochem Behavior* 62, 743-751 (1999)). Rats were treated with test compounds I-7. At 15 mg/kg, i.p., 1-7 showed decreased nicotine self-administration ranging from 14 to 33% in IVSA of nicotine (Table 4). Certain compounds (i.e., 2, 5 and 6) tested in rats at 25 mg/kg showed decreases in nicotine self-administration ranging from 60 to 85% in IVSA of nicotine (Table 4). Based on these results, compounds 8-11 and mecamylamine (as a positive control) were examined in more detail. Mecamylamine (3.0 mg/kg, s.c., 30 minutes before the session) decreased nicotine self-administration under a FR1 schedule of reinforcement ANOVA of this data revealed a significant decrease in the number of nicotine infusions during 1-hour self-administration sessions (F=11.9, df 1, 7, p<0.02). At 3.0 mg/kg, responding for nicotine was decreased by 62% when compared to control (vehicle-treated) conditions. A comparison of Tables 1 and 4 showed no clear relationship between potency of human CYP 2A6 inhibition determined in vitro on the basis of kinetic studies of selective functional substrates and percent decrease in nicotine self-administration in vivo. For example, the potent human CYP 2A6 inhibitor 3 (i.e., K, =0.08 μM) afforded a similar decrease in nicotine self-administration in the IVSA studies as the inactive (i.e., K$_i$>200 μM) human CYP 2A6 inhibitor 7 (i.e., 23.6% versus 28.6% decrease in nicotine self-administration, (Table 4). Despite this result, there were several SAR observations that emerged from the initial study of compounds I-7 including: 1) certain small nucleophilic nicotine analogs decreased nicotine self-administration, 2) compounds that possessed a 3-heteroaromatic pyridine (i.e., 4-7) were effective but analogs without a 3-pyridine (i.e., 3) were also effective at decreasing nicotine self-administration, and 3) complex 3-heteroaromatic moieties could be replaced with a simple imidazole group and retain in vivo pharmacological efficacy (i.e., 6 vs. 7). On the basis of these initial studies, more extensive work was done and IVSA studies of compounds 8, 10 and 11 were conducted.

TABLE 4

Effect of Compounds 1-7 on Nicotine Self-Administration

| # | Structure | Vehicle[a] | Compound[a] (15 mg/kg) | % Change | Vehicle | Compound[a] (25 mg/kg) | % Change | N[b] |
|---|---|---|---|---|---|---|---|---|
| 1 | 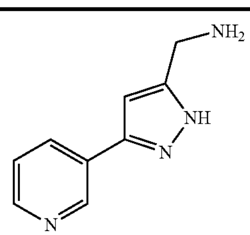 | 13.6 ± 2.6 | 11.6 + 2.9 | 14.7 | NA[c] | NA |  | 5 |

TABLE 4-continued

Effect of Compounds 1-7 on Nicotine Self-Administration

| # | Structure | Vehicle[a] | Compound[a] (15 mg/kg) | % Change | Vehicle | Compound[a] (25 mg/kg) | % Change | N[b] |
|---|---|---|---|---|---|---|---|---|
| 2 | 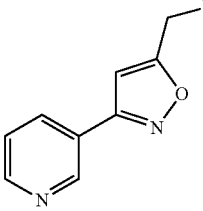 | 10.4 + 2.7 | 8.4 + 1.7 | 19.2 | 14.0 + 3.3 | 5.6 + 1.6[d] | 60. | 5 |
| 3 | 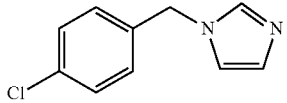 [SMILES: Clc1ccc(Cn2ccnc2)cc1] | 10.8 + 3.2 | 13.0 + 2.7 | 23.6 | NA | NA | | 5 |
| 4 | 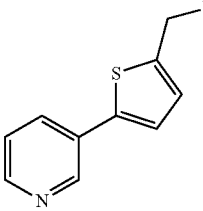 | 15.4 + 1.5 | 11.8 + 3.2 | 23.4 | NA | NA | | 5 |
| 5 | 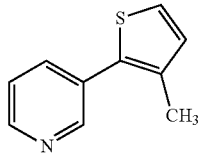 | 13.2 + 2.5 | 8.8 + 1.6 | 33.3 | 10.4 + 3.1 | 1.6 + 0.7[d] | 84.6 | 5 |
| 6 | 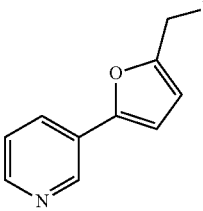 | 23.2 + 1.8 | 16.8 + 2.3[d] | 27.6 | 23.2 + 1.8 | 8.3 + 2.1[d] | 64.2 | 8 |
| 7 | 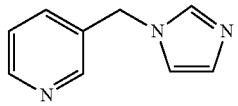 [SMILES: c1cncc(Cn2ccnc2)c1] | 10.5 + 1.3 | 7.5 + 1.9[d] | 28.6 | NA | NA | | 8 |

[a]Number refers to the effects of the vehicle or compound (15.0 mg/kg or 25 mg/kg), i.p. 30 minutes before i.v. self-administration of 0.03 mg/kg/infusion of nicotine under a FR1 schedule of reinforcement as described in the Methods.
[b]N is the number of animals used in the self-administration study test group.
[c]NA, Not Available.
[d]Statistically different than vehicle-treated animals (p = 0.05).

Example 6

Effect of Compounds 8-11 on Nicotine Self-Administration

Figure 2:
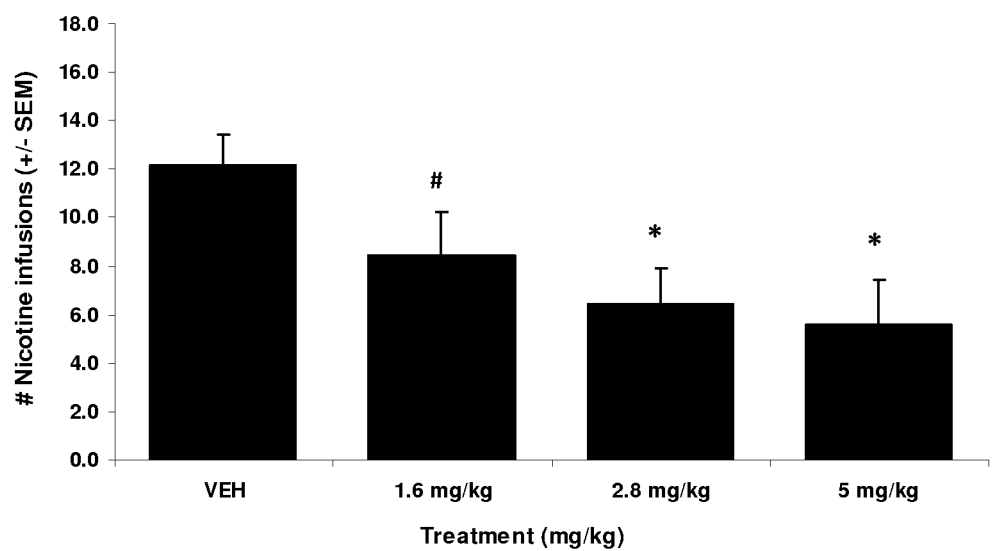
FIG. 2 is a graph showing the effects of compound II on IV self-administration of 0.03 mg/kg/infusions of nicotine under a FR1 schedule of reinforcement. Data are expressed as mean (±S.E.M.) number of infusions per session (n=7 rats). An ANOVA of the dose response of compound II revealed a significant effect of 11 on nicotine intake (F=7.3, df 3, 21, p=0.0021). Follow-up analysis (paired t-test) of individual doses of 11 revealed that doses of 2.8 and 5 mg/kg were significantly different from vehicle-treated rats. There was a near-significant effect of 1.6 mg/kg of 11 (#, p=0.06). *, p<0.05.

The dose-effect function for 8 on nicotine IVSA showed that at stable criteria, rats responded with an average of 18.5±1.7 infusions (data not shown), that was not significantly different from the 0 (zero) dose within the Latin square design (average vehicle dose value=23.5±3.1). An ANOVA of the treatment data (i.e., compound 8 dose response) failed to reveal a significant effect of 8 on nicotine intake during 1-hour self-administration sessions (F=2.81, df 3, 21, p=0.0644), although the analysis did reveal a "near significant effect". As with all the compounds examined in this study, there was no carry-over effect. That is, there was no residue effect 24 hr after administration of 1-11 indicating that whatever effect that caused blockade of nicotine self-administration was not irreversible. Pretreatment with compound 9 (15 mg/kg, i.p., 30-min prior) decreased nicotine self-administration under a FR schedule (F=16.8, df 1, 7, p=0.0046). Pretreatment with compound 10 [FIG. 1] revealed a significant effect of 10 on IVSA of nicotine (F=15.5, df 3, 21, p<0.0001). Post-hoc analysis of individual doses of 10 revealed that the dose of 5 mg/kg was significantly different from control (vehicle-treated) conditions, with a corresponding p-value of <0.0001. Pretreatment with compound II (i.p. administration, 30 min before the session) significantly decreased nicotine self-administration under an FR schedule. The dose-effect function for treatment of 11 on nicotine self-administration is shown in [FIG. 2]. An ANOVA of the dose response of 11 revealed a significant effect of 11 on nicotine intake (F=7.3, df 3, 21, p=0.0021). Follow-up analysis (paired t-test) of individual doses of 11 revealed that doses of 2.8 and 5 mg/kg were significantly different from control (vehicle-treated) conditions, with corresponding p-values of 0.0017 and 0.009, respectively. There was a near-significant effect of 1.6 mg/kg of 11 on nicotine intake (p=0.06).

Example 7

Order and Food effects of Compounds 10 and 11 on IVSA of Nicotine

The effect of the two most potent compounds was examined for effects on food intake using operant techniques. Table 5 shows the effects of compounds 10 and 11 on food intake during 30-min operant food sessions. Results revealed that there was no effect of drug dose order within the repeated measures dose design. Furthermore, results revealed that only the largest dose of compound 11 (i.e., 5 mg/kg) produced a significant suppression on food intake. The conclusion is that the effect of 10 and 11 was selective and highly efficacious on a biological target and not a promiscuous non-specific behavioral effect.

TABLE 5

Order and Food effects of 10 and 11 on self-administration of nicotine in rats

| Compound 10 | | | | |
|---|---|---|---|---|
| Order Effects | Day 1 | Day 2 | Day 3 | Day 4 |
| | 75 ± 3.3[a] | 78 ± 1.7 | 79 ± 3.2 | 80 ± 1.9 |
| Food Effects | Dose[b] | Dose | Dose | Dose |
| | Vehicle | 0.5 | 1.58 | 5.0 |
| | 77 ± 3.0 | 80 ± 1.8 | 79 ± 2.5 | 77 ± 3.2 |
| Compound 11 | | | | |
| Order Effects | Day 1 | Day 2 | Day 3 | Day 4 |
| | 76 ± 4.1 | 78 ± 2.3 | 76 ± 3.7 | 71 ± 4.8 |
| Food Effects | Dose[a] | Dose | Dose | Dose[c] |
| | Vehicle | 1.6 | 2.8 | 5.0 |
| | 79 ± 1.0 | 81 ± 1.2 | 79 ± 1.3 | 63 ± 5.6 |

[a]Average number of nicotine self-administrations in one hour ± SEM;
[b]Dose, mg/kg;
[c]Statistically different than vehicle-treated animals (p < 0.05).

Summary for Examples 1-6

An efficient method for synthesizing the analogs of nicotine was accomplished. The design of the molecules was to incorporate functional groups into the molecules that would ligate to the prosthetic heme iron of CYP2A6—the enzyme that predominantly oxidizes nicotine. The synthetic compounds were evaluated as inhibitors of coumarin 7-hydroxylase activity using a fluorescence assay. Compounds with significant inhibitory activity were next evaluated for inhibition of other CYPs. None of the analogs were found to be a highly potent at inhibiting other CYPs and were thus selective inhibitors of CYP2A6. Very potent and less potent CYP2A6 inhibitors were examined for decrease in IVSA of nicotine. Compound efficacy did not exactly parallel with CYP2A6 inhibitory potency. Compounds 1-11 did not potently inhibit Rat 2B1 (the major nicotine metabolizing enzyme in rats) nor did analogs examined decrease the AUC for nicotine metabolism in vivo. Accordingly, CYP2B1 in the rat is not the target for the mechanism of action. Because no direct binding to mammalian nAChRs or hDAT was observed for the test compounds examined, these are not the target for mechanism of direct action, either although the compounds may be acting indirectly. Compounds 1-11 were studied in a nicotine IVSA paradigm as a model of human smoking to examine if the compounds caused a decrease in nicotine self-administration. Compounds 10 and 11 were highly efficacious with apparent ED50 values of 4 and 3 mg/kg, respectively. Currently, the biological target is unknown but the drug discovery paradigm has resulted in highly potent compounds that are very efficacious at decreasing IVSA of nicotine in rats.

The approach has lead to active compounds with promising pharmacological properties that could lead to a new class of smoking harm reduction agents and lung cancer inhibitors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating nicotine addiction comprising administering an effective amount of a compound to a subject in need thereof, wherein the compound has the structure of

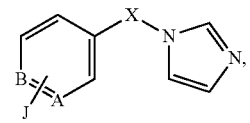

or a pharmaceutically acceptable salt thereof,
wherein one of A and B is nitrogen and the other is carbon
J is halogen or —H; and
X is —CH$_2$— or —CH$_2$CH$_2$—.

2. The method of claim 1 wherein A is nitrogen and B is carbon.

3. The method of claim 2 wherein X is —CH$_2$— and J is —H or —Cl.

4. The method of claim 2 wherein X is —CH$_2$CH$_2$— and J is —H.

5. The method of claim 1 wherein the compound is N-(3-Pyridylmethyl)imidazole.

* * * * *